(12) United States Patent
Woelfert et al.

(10) Patent No.: US 8,173,833 B2
(45) Date of Patent: May 8, 2012

(54) METHOD FOR THE PRODUCTION OF ISOCYANATES

(75) Inventors: Andreas Woelfert, Bad Rappenau (DE); Andreas Daiss, Deidesheim (DE); Torsten Mattke, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/513,864

(22) PCT Filed: Nov. 6, 2007

(86) PCT No.: PCT/EP2007/061931
§ 371 (c)(1),
(2), (4) Date: May 7, 2009

(87) PCT Pub. No.: WO2008/055898
PCT Pub. Date: May 15, 2008

(65) Prior Publication Data
US 2010/0041914 A1    Feb. 18, 2010

(30) Foreign Application Priority Data
Nov. 7, 2006  (EP) .................................. 06123631

(51) Int. Cl.
*C07C 263/00*  (2006.01)
(52) U.S. Cl. ................................................... 560/347
(58) Field of Classification Search .................. None
See application file for complete search history.

(56) References Cited

U.S. PATENT DOCUMENTS

| | | | | |
|---|---|---|---|---|
| 4,128,569 A | * | 12/1978 | Horn et al. | 560/347 |
| 4,289,732 A | * | 9/1981 | Bauer et al. | 422/224 |
| 4,581,174 A | * | 4/1986 | Ohlinger et al. | 560/347 |
| 2002/0132953 A1 | * | 9/2002 | Strofer et al. | 528/44 |
| 2004/0118672 A1 | * | 6/2004 | Grun et al. | 203/29 |
| 2004/0167354 A1 | | 8/2004 | Biskup et al. | |
| 2005/0159290 A1 | | 7/2005 | Yamamoto et al. | |
| 2006/0089507 A1 | * | 4/2006 | Sohn et al. | 560/347 |
| 2006/0252960 A1 | * | 11/2006 | Sohn et al. | 560/347 |
| 2009/0221846 A1 | * | 9/2009 | Wolfert et al. | 560/347 |
| 2010/0048942 A1 | * | 2/2010 | Knoesche et al. | 560/347 |

FOREIGN PATENT DOCUMENTS

| | | | |
|---|---|---|---|
| DE | 1792660 | * | 3/1972 |
| DE | 103 59 627 | | 7/2005 |
| EP | 0 928 785 | | 7/1999 |
| EP | 1 275 639 | | 1/2003 |
| EP | 1 275 640 | | 1/2003 |
| EP | 1 449 826 | | 8/2004 |
| EP | 1 555 248 | | 7/2005 |
| WO | 02 02217 | | 1/2002 |
| WO | 2007 028715 | | 3/2007 |

OTHER PUBLICATIONS http://en.wikipedia.org/wiki/Phase_(matter).*
U.S. Appl. No. 12/675,137, filed Feb. 25, 2010, Olbert, et al.
U.S. Appl. No. 12/675,187, filed Feb. 25, 2010, Olbert, et al.
U.S. Appl. No. 12/678,771, filed Mar. 18, 2010, Knoesche, et al.
U.S. Appl. No. 13/001,681, filed Dec. 28, 2010, Knoesche, et al.

* cited by examiner

*Primary Examiner* — Daniel Sullivan
*Assistant Examiner* — Jennifer C Sawyer
(74) *Attorney, Agent, or Firm* — Oblon, Spivak, McClelland, Maier & Neustadt, L.L.P.

(57) ABSTRACT

The present invention relates to a process for preparing isocyanates.

25 Claims, 7 Drawing Sheets

METHOD FOR THE PRODUCTION OF ISOCYANATES

The present invention relates to a process for preparing isocyanates.

To prepare isocyanates by phosgenation of the corresponding amines, it is in principle possible to employ liquid-phase or gas-phase phosgenation. In gas-phase phosgenation, the reaction conditions are selected so that at least the reaction components diamine, diisocyanate and phosgene, but preferably all starting materials, products and reaction intermediates, are gaseous under these conditions. The present invention relates exclusively to gas-phase phosgenation.

EP 1 275 639 A1 describes the gas-phase phosgenation of (cyclo)aliphatic diamines in a reaction zone having constrictions of the walls.

In the mixing device, the amine- and phosgene-comprising feed streams are fed coaxially into a mixing zone, with the phosgene-comprising feed stream being fed in in the middle and the amine-comprising feed stream being fed in around the outside. In the region where the feed streams are combined, there is a further reduction or a slight enlargement of the flow cross section, so that the flow velocity increases over the course of the reaction as a result of the increasing volume.

A disadvantage of this arrangement is that the amine stream is conveyed coaxially on the outside. This can result in solids formation on the walls of the mixing device, since the amine is present in excess over the phosgene at the walls, which favors by-product formation. A further disadvantage of the process is that when the flow is accelerated too much by the narrowing of the cross section, this results in damping of the turbulent fluctuating velocities in the stream which are critical for rapid mixing in a turbulent stream.

It is likewise stated in EP 1 275 639 A1 that twisting of the feed streams should occur before the feed streams are combined, so that the turbulent fluctuating velocities in the feed streams are increased and mixing then occurs more rapidly when the two feed streams are combined.

However, a disadvantage is that the increase in the fluctuating velocities also increases the dispersion of the stream at the point at which the amine-comprising feed stream enters the mixing zone and thus increases the risk of blockage of the mixing nozzle.

EP 1 275 640 A1 describes the gas-phase phosgenation of (cyclo)aliphatic diamines and triamines in a mixing tube with reactor, in which the gas stream is accelerated in the mixing region. A reactor geometry having an inner tube and an outer tube by means of which a gas-phase phosgenation on a scale of only about 211 g of hexamethylene-1,6-diamine per hour is possible is disclosed.

A disadvantage of this process is that the maximum velocity difference between the reactant streams is not reached immediately at the beginning of mixing and the minimum possible mixing time is therefore also not achieved.

A disadvantage of the reactors disclosed in these two documents is that if this reactor geometry were to be simply scaled up to industrially feasible sizes, the diameter of the inner tube would have to be increased to such an extent that mixing of the streams fed through the two tubes would no longer be possible in short mixing times because of the long distances perpendicular to the flow direction.

EP 928 785 A1 describes a process for preparing isocyanates by means of a mixing device which comprises a plurality of microstructural mixing elements. However, the process suffers from the disadvantage of the very small free cross sections of the individual amine and phosgene feed lines which are particularly susceptible to deposition of solids and blockages.

EP 1 449 826 A1 discloses a predistribution of the amine-comprising stream over at least two individual amine inlets. However, these are hydrodynamically decoupled from one another. If the cross section of one of these tubes is decreased, for example as a result of formation of amine hydrochlorides, the throughput through this tube is automatically reduced because of the increase in the pressure drop so that the flow through the tube is decreased. However, smaller throughputs lead to even more solids being deposited on the wall, so that blockage proceeds even more quickly. A disadvantage here is that the residence time distribution of the stream of mixture is relatively broad because of the large cross section after introduction relative to the length of the reaction zone.

DE 10359627 A1 discloses a gas-phase phosgenation in which the amine is mixed in through a concentric annular gap between two phosgene streams, with the areas through which the phosgene streams flow having a ratio of from 1:0.5 to 1:4.

A disadvantage of this reactor geometry, too, is that if the reactor geometry is simply scaled up to industrially feasible sizes, the internal diameter of the mixing device can be increased only to a particular limit while adhering to this area ratio.

WO 02/02217 describes various processes for mixing feed streams, including streams for liquid-phase phosgenation.

A disadvantage is that the processes disclosed there for mixing liquid phases are designed for low entry velocities of only about 10 m/s, while the significantly higher velocities required in gas-phase phosgenations and the mixing of gases have other hydrodynamic requirements than the mixing of liquids. In addition, the reaction rates of phosgenation in the gas phase are significantly different from those in the liquid phase, so that the process of WO 02/02217 cannot be transferred readily to the gas phase.

WO 2007/028715 discloses a process in which amine and phosgene are introduced via an annular gap, i.e. a gap enclosed in the form of an annulus.

It was accordingly an object of the present invention to develop a method of carrying out a gas-phase phosgenation reaction, which makes it possible to carry out the reaction on an industrial scale and brings at least one of the following advantages:

shorter mixing path lengths made possible
no or only very little backmixing
not susceptible to blockages as a result of only a low tendency for solid deposits to be formed
advantageous residence time distribution.

This object is achieved by a process for preparing isocyanates by reacting the corresponding amines with phosgene, if appropriate in the presence of at least one, preferably precisely one, inert medium, in the gas phase, which comprises reacting n amine streams with at least n phosgene streams, where n is a positive integer of at least 1, in a reactor and introducing at least one amine or phosgene stream into the reactor via at least one slit for mixing.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 3, depiction a), shows the area F through which flow occurs does not change along the reactor;

FIG. 3, depiction b), shows the area $F_1$ through which flow occurs enlarges in a section 1 directly after the streams have been combined and then remains constant in a second section 2;

FIG. 3, depiction c), shows the area $F_1$ remaining constant in a section 1 and widens in the second section before remaining constant again in the third section;

FIG. 3, depiction d), shows the area $F_1$ is kept constant in a section 1, $F_2$ in the section 2 is then reduced and $F_3$ is increased in section 3 and is kept constant in section 4;

FIG. 3, depiction e), shows the area $F_1$ is reduced in a first section, $F_2$ is increased in the second section and $F_3$ is kept constant in the third section; and FIG. 3, depiction f), shows the area $F_1$ is reduced, remains constant in section two, is increased again in section 3 and then remains constant again in the fourth section.

In WO 2007/028715, the terms "annular gap" and "annular gap space" are used as follows:

The annular gap space is thought of as a generalization of a hollow cylinder (for the definition of a hollow cylinder, see Bronstein, "Taschenbuch der Mathematik", 21st edition, p. 199): an annular gap space is the volume enclosed by an outer and an inner, in each case spatially curved, closed surface and the bounding end faces, with the two curved surfaces not intersecting.

The annular gap is thought as a generalization of an annulus (for the definition of an annulus, see Bronstein, "Taschenbuch der Mathematik", 21st edition, p. 194): the annular gap has the shape of the end face which bounds the above-described annular gap space at its end.

On the other hand, the term "slit" as used in the present text is an area which is not connected in the form of an annulus; instead, a "slit" is a simply contiguous area. Such slits can, according to the invention, have any shape as long as they are not connected in the form of an annulus. Examples of possible shapes are linear, wave-shaped, zig-zag or loop-shaped slits, with preference being given to the slits being linear.

The phosgene- and amine-comprising feed streams to be introduced into the mixing chamber in the process enter the mixing chamber on one side through at least (2n), for example two, two-dimensional slits. Various possible embodiments are conceivable here:

The slits can be stacked one above the other. In this case, for example, a slit through which the amine is introduced is flanked on both long sides by preferably parallel slits through which the phosgene is introduced. These can in turn be flanked in the same way by two slits for introduction of amine which can in turn be flanked by two slits through which phosgene is introduced.

This results in a stack of (2n+1) slits, with phosgene preferably being introduced through the outer slits.

Figure 1A:
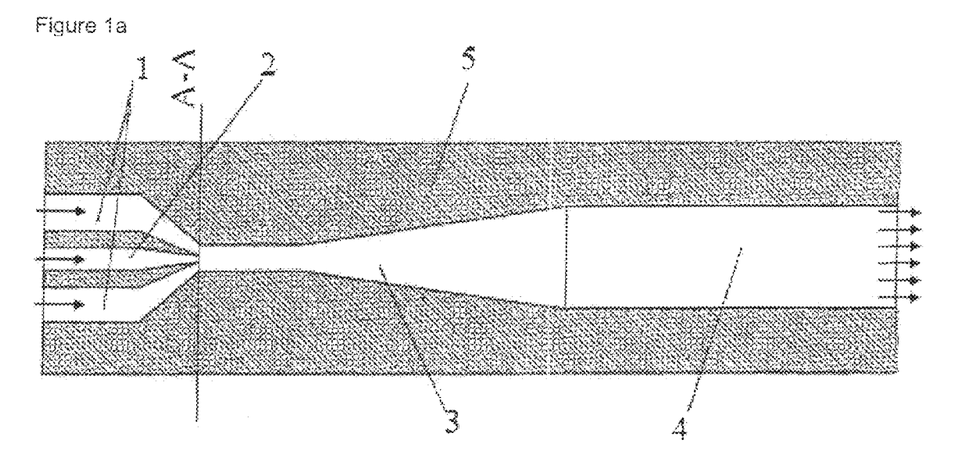
FIGS. 1a and 1b illustrate embodiments where amine is introduced through an inner slit which is surrounded on all sides by a contiguous, for example rectangular, slit through which phosgene is introduced.
Figure 1B:
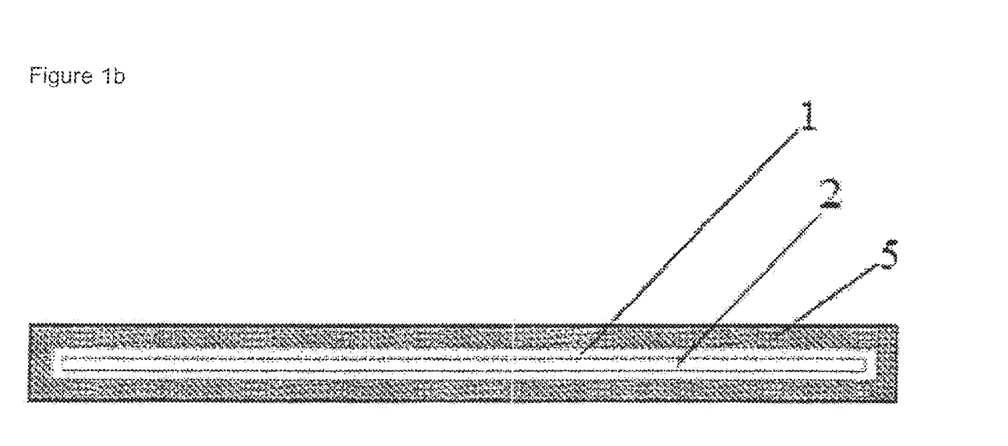

In a further embodiment, amine is introduced through an inner slit which is surrounded on all sides by a contiguous, for example rectangular, slit through which phosgene is introduced (FIGS. 1a and 1b). This can, for example, then be flanked by a further contiguous or noncontiguous slit for introduction of amine which is in turn surrounded on all sides by a contiguous, for example rectangular, slit through which phosgene is introduced.

This gives a preferred arrangement in which a slit is surrounded by a contiguous slit.

To avoid deposition of solids and blockages, the phosgene-comprising feed stream is, in the case of the mixing device according to the invention, preferably conveyed so that the phosgene-comprising feed stream or streams flows over all apparatus walls after the feed streams have been combined and the amine-comprising feed stream or streams is surrounded completely by the phosgene-comprising feed stream or streams until complete mixing of the streams or largely complete reaction of the amine has occurred.

The amine is therefore preferably introduced on the inside via a slit which is surrounded completely, i.e. not only above and below but also on the sides, by a phosgene stream. This surrounding, contiguous slit is then matched to the shape of the slit, i.e., for example, in the case of a linear slit for the introduction of amine, by a rectangular inlet for phosgene (see FIG. 1b).

The amines which can be used in a gas-phase phosgenation have to meet particular requirements (see below).

They can be monoamines, diamines, triamines or higher-functionality amines, preferably diamines. The phosgenation accordingly gives the corresponding monoisocyanates, diisocyanates, triisocyanates or higher-functionality isocyanates, preferably diisocyanates.

The amines and isocyanates can be aliphatic, cycloaliphatic or aromatic, preferably aliphatic or cycloaliphatic and particularly preferably aliphatic.

Cycloaliphatic isocyanates are ones which comprise at least one cycloaliphatic ring system.

Aliphatic isocyanates are ones which have exclusively isocyanate groups which are bound to straight or branched chains.

Aromatic isocyanates are ones which have at least one isocyanate group bound to at least one aromatic ring system.

The expression (cyclo)aliphatic isocyanates is, for the purposes of the present patent application, an abbreviation for cycloaliphatic and/or aliphatic isocyanates.

Examples of aromatic diisocyanates are preferably those having 6-20 carbon atoms, for example monomeric 2,4'- or 4,4'-methylenedi(phenyl isocyanate) (MDI), tolylene 2,4- and/or 2,6-diisocyanate (TDI) and naphthylene 1,5- or 1,8-diisocyanate (NDI).

Diisocyanates are preferably (cyclo)aliphatic diisocyanates, particularly preferably (cyclo)aliphatic diisocyanates having from 4 to 20 carbon atoms.

Examples of customary diisocyanates are aliphatic diisocyanates such as tetramethylene 1,4-diisocyanate, pentamethylene 1,5-diisocyanate, hexamethylene diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, derivatives of lysine diisocyanate, tetramethylxylylene diisocyanate (TMXDI), trimethylhexane diisocyanate or tetramethylhexane diisocyanate and 3 (or 4), 8 (or 9)-bis(isocyanatomethyl)tricyclo[5.2.1.0$^{2.6}$]decane isomer mixtures and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3, 5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane. Preference is given to pentamethylene 1,5-diisocyanate, 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures. Particular preference is given to 1,6- diisocyanatohexane, 1-isocyanato-3,3,5-trimethyl-5-(isocyanatomethyl)cyclohexane and 4,4'-di(isocyanatocyclohexyl)methane.

In the process of the invention, the reaction of amines to form the corresponding isocyanates can be carried out using amines in the case of which the amine, the corresponding intermediates and the corresponding isocyanates are gaseous under the reaction conditions selected. Preference is given to amines which decompose under the reaction conditions to an extent of not more than 2 mol %, particularly preferably not more than 1 mol % and very particularly preferably not more than 0.5 mol %, during the time of the reaction. Particularly useful amines here are amines, in particular diamines, based on aliphatic or cycloaliphatic hydrocarbons having from 2 to 18 carbon atoms. Examples are 1,5-diaminopentane, 1,6-diaminohexane, 1-amino-3,3,5-trimethyl-5-aminomethylcyclohexane (IPDA) and 4,4'-diaminodicyclohexylmethane. Preference is given to using 1,6-diaminohexane (HDA).

It is likewise possible to use aromatic amines which can be brought into the gas phase without significant decomposition for the process of the invention. Examples of preferred aromatic amines are toluenediamine (TDA) as 2,4- or 2,6-isomer or a mixture thereof, for example as a from 80:20 to 65:35 (mol/mol) mixture, diaminobenzene, 2,6-xylidine, naphthalene diamine (NDA) and 2,4'- or 4,4'-methylenedi(phenylamine) (MDA) or isomer mixtures thereof. Among these, preference is given to the diamines, particularly preferably 2,4- and/or 2,6-TDA.

In gas-phase phosgenation, it is by definition desirable for the compounds occurring during the course of the reaction, i.e. starting materials (diamine and phosgene), intermediates (in particular the monocarbamyl and dicarbamyl chlorides formed as intermediates), end products (diisocyanate) and any inert compounds introduced, to remain in the gas phase under the reaction conditions. Should these or other components deposit from the gas phase, e.g. on the reactor wall or other components of the apparatus, these deposits can result in undesirable changes in heat transfer or flow through the apparatus components concerned. This applies particularly to amine hydrochlorides which are formed from free amino groups and hydrogen chloride (HCl), since the resulting amine hydrochlorides precipitate easily and can be vaporized again only with difficulty.

The starting materials, or else only one of them, can be introduced together with at least one inert medium into the mixing space.

The inert medium is a medium which is present in gaseous form in the reaction space at the reaction temperature and does not react with the compounds occurring during the course of the reaction. The inert medium is generally mixed with amine and/or phosgene prior to the reaction, but can also be introduced separately from the feed streams. For example, it is possible to use nitrogen, noble gases such as helium or argon, or aromatics such as chlorobenzene, chlorotoluene, o-dichlorobenzene, toluene, xylene, chloronaphthalene, decahydronaphthalene, carbon dioxide or carbon monoxide. Preference is given to using nitrogen and/or chlorobenzene as inert medium.

The inert medium is generally used in such an amount that the ratio of the gas volumes of inert medium to amine or to phosgene is from >0.0001 to 30, preferably from >0.01 to 15, particularly preferably from >0.1 to 5.

The starting amines are vaporized and heated to from 200° C. to 600° C., preferably from 300° C. to 500° C., before carrying out the process of the invention and are, if appropriate, diluted with an inert gas or with the vapor of an inert solvent before being fed through the mixing device into the reactor.

The phosgene used in the phosgenation is, if appropriate, diluted with an inert gas or with the vapor of an inert solvent and likewise heated to a temperature in the range from 200° C. to 600° C., preferably from 300° C. to 500° C., before carrying out the process of the invention.

In a preferred embodiment, the n amine streams are heated to a temperature which is up to 50° C. higher than that of the (n+1) phosgene streams, preferably to a temperature which is up to 30° C., particularly preferably up to 24° C. and very particularly preferably up to 20° C., higher. The temperature of the n amine streams is preferably at least 5° C., particularly preferably at least 10° C., above that of the (n+1) phosgene streams.

According to the invention, phosgene is used in an excess over amino groups. The molar ratio of phosgene to amino groups is usually from 1.1:1 to 20:1, preferably from 1.2:1 to 5:1.

In the process of the invention, mixing and reaction of the two gaseous starting materials takes place after introduction of the feed streams diamine and phosgene via the slits as entry areas into the mixing space as reaction space.

The reaction generally commences with contact of the starting materials immediately after mixing.

Thus, mixing of the starting materials, if appropriate mixed with inert medium, takes place in the front part of the reaction space (mixing space).

To carry out the reaction according to the invention, the preheated stream comprising amine or mixtures of amines and the preheated stream comprising phosgene are fed continuously into the reactor, preferably a tube reactor.

The reactors generally comprise steel, glass, alloy steel or enameled steel and have a length which is sufficient to make complete reaction of the diamine with the phosgene possible under the process conditions.

Mixing Device

The (n+1) phosgene streams and n amine streams are generally fed into a residence reactor via a mixing unit at one end of the reactor. Between each two phosgene streams, an amine stream is fed in via a slit at a high velocity. The introduction of all phosgene streams and amine streams is in each case effected via slits in a stack of slits. Each slit is preferably surrounded by an appropriate facility for introducing the other reaction component (see FIG. 1b). The slits by means of which adjacent phosgene streams and the amine stream located in between are fed in are preferably configured in such a way that the inner amine stream is completely surrounded by a phosgene stream.

In one embodiment, these can then in turn be surrounded concentrically by further introduction facilities.

The slits preferably have a ratio of width to height of at least 2:1, preferably at least 3:1, particularly preferably at least 4:1, very particularly preferably at least 5:1 and in particular at least 10:1. An upper limit is imposed on the ratio of width to height only by constructionally sensible and practicable values. In general, the ratio is less than 500:1, preferably less than 250:1 and particularly preferably less than 100:1.

The width and height are in each case based on the greatest width and the greatest height of the slit.

The two-dimensional shape of the slits is preferably rectangular, but diamond shapes, trapezoids, ovals, ellipses and shapes tapering to the side, for example slits having a hexagonal cross section or eye-shaped areas, are also conceivable.

It can be useful to install flow equalizers as are known, for example, from EP 1362847 A in the feed lines. However, the velocity of the feed streams is preferably equalized by a fore-run length in the feed line whose length is from 2 to 40 times, particularly preferably from 4 to 30 times, very particularly preferably from 5 to 20 times, the diameter of the feed line.

A narrowing of the flow cross section after the feed streams have been combined, as described in EP 1275640A1, in order to avoid backmixing is possible but can preferably be omitted.

According to the invention, a very short transverse diffusion distance over which the fluid elements are exchanged by turbulent and laminar diffusion and thus effect mixing is critical for mixing of the streams. Whereas in DE 103 59 627 A1 the amine stream is introduced via a double-walled guide tube forming an annular gap, only the outer one of the two phosgene streams is introduced via an annular gap, namely via a "cross-sectional area which is bounded by the wall of the tube reactor and the outer wall of the double-walled guide tube" while the inner phosgene stream is introduced via the "cross-sectional area bounded by the inner wall of the double-walled guide tube", i.e. via a circular area. Thus, following the teachings of DE 103 59 627 A1, the transverse diffusion distance between the inner phosgene stream and the amine stream increases when the cross section of the reactor or the inner phosgene inlet is increased.

According to the invention, the amine stream is mixed in via a slit between two phosgene streams which are in turn introduced via slits. This principle of the invention can be generalized analogously for the introduction of n amine streams, for example 2, 3, 4 or more, in each case between two layers of (n+1) phosgene streams. n is preferably 1, 2 or 3, particularly preferably 1 or 2 and very particularly preferably 1.

For an amine stream not to have any contact with the walls of the apparatus in accordance with the inventive concept after commencement of mixing but instead to be surrounded by phosgene-comprising feed streams, the amine stream is introduced in a "sandwich-like fashion" between two phosgene streams.

This means, according to the invention, that the uppermost and the bottommost or outermost stream is in each case a phosgene stream which keeps the amine stream or streams away from the walls of the reactor.

The flow cross sections of the phosgene-comprising feed stream or streams are dimensioned so that the characteristic mixing dimension is again very small. Since the starting material phosgene is fed in in a stoichiometric excess and the phosgene velocity is also preferably less than the amine velocity, a larger cross-sectional area than for the amine-comprising stream has to be selected, which also results in larger characteristic dimensions. The mixing path length becomes less than 200 mm, preferably less than 100 mm, particularly preferably less than 50 mm, very particularly preferably less than 25 mm and in particular less than 10 mm. The mixing path length is defined as the maximum distance which the fluid elements of two or more feed streams have to cover perpendicular to the flow direction of the feed streams before molecular mixing of the feed streams is complete.

The ratio of the total area of the amine streams to the total area of the phosgene streams is greater than 0.00002, preferably greater than 0.0002, particularly preferably greater than 0.002 and very particularly preferably greater than 0.02.

The ratio of the total area of the amine streams to the total area of the phosgene streams is less than 5, preferably less than 1, particularly preferably less than 0.5 and very particularly preferably less than 0.2.

The area ratio of two phosgene-conveying areas which are separated by an amine-conveying slit is from 0.1 to 10, preferably from 0.2 to 5, particularly preferably from 0.4 to 2.5, very particularly preferably from 0.8 to 1.25, in particular from 0.9 to 1.1 and especially 1.

At $n \geq 2$, the area ratio of two amine-conveying areas which are separated by a phosgene-conveying area is from 0.1 to 10, preferably from 0.2 to 5, particularly preferably from 0.4 to 2.5, very particularly preferably from 0.8 to 1.25, in particular from 0.9 to 1.1 and especially 1.

Since the intensity and rapidity of mixing of the amine- and phosgene-comprising feed streams depend essentially on the shear rate established in the mixing zone, the mixing zone has to be configured so that the shear rate is particularly large.

For this purpose, the velocity difference between the amine- and phosgene-comprising feed streams should be selected so as to be particularly high and, in addition, the characteristic dimensions should be selected so as to be very small, since the shear rate is proportional to the ratio of velocity difference to characteristic dimension.

Since the velocity difference between the amine- and phosgene-comprising feed streams should be high, either the phosgene-comprising feed streams or the amine-comprising feed streams have to have a greater velocity. Since the feed lines for amine to the mixing zone are more sensitive to formation of deposits and blockages and backflow into the amine inlet has to be avoided at all costs, the flow velocity of the amine-comprising feed stream is preferably made greater than the velocity of the phosgene-comprising feed stream.

The higher the velocity of the amine-comprising feed streams, the higher can the velocity of the phosgene-comprising feed streams be for the same shear rate. A higher phosgene velocity results in smaller flow cross sections of the phosgene inlet and thus smaller mixing path lengths and thus more rapid mixing.

To achieve a very high amine velocity, efforts are therefore made to set a local Mach number of greater than 0.6 in the amine stream at the point where it is combined with the phosgene stream.

The Mach number is the ratio of the local flow velocity to the local speed of sound. In a particular embodiment of the process, the amine-comprising feed streams are introduced in such a way that the Mach number at the outlet of the amine streams into the mixing zone is 1.

In the case of a matched introduction of amine, the pressure of the amine stream at this point corresponds to the pressure of the phosgene-comprising feed stream at the point where the streams are combined. In the case of an unmatched introduction of amine, the pressure of the amine stream at the exit from the amine inlet is greater than the pressure of the phosgene-comprising stream at the point where the streams are combined. In this case, further expansion of the amine-comprising stream occurs, which is associated with a decreasing pressure down to the pressure of the phosgene-comprising stream.

Whether a nozzle is operated in a matched or unmatched fashion depends on the admission pressure of the amine-comprising stream and the phosgene-comprising stream upstream of the mixing nozzle.

In a further particular embodiment, the amine inlet is configured so that Mach numbers of greater than 1 are already reached in the inlets. This can be achieved, for example, by the inlet for the amine-comprising streams being configured in the form of one or more Laval nozzles in which the flow cross section initially narrows until a Mach number of 1 is reached and then widens again, which leads to further expansion and acceleration of the stream. To achieve supersonic flow (Mach number greater than 1), the ratio of the amine boiler pressure to the mixing zone pressure has to be greater than the critical pressure ratio. The higher the pressure ratio and the higher the boiler temperature of the amine stream, the higher the maximum velocity which can be achieved.

However, since the starting material amine is often thermally damaged at temperatures which are too high, excessively high temperatures must not be set. In addition, the amine admission pressure can also not be increased at will due to the amine vapor pressure.

The amine is therefore preferably introduced in such a way that Mach numbers of from 0.6 to 4, particularly preferably from 0.7 to 3, very particularly preferably from 0.8 to 2.5 and in particular from 0.9 to 2.0, are obtained in the amine-comprising feed stream directly at the point at which it is combined with the phosgene-comprising stream or in the case of an unmatched nozzle shortly thereafter.

The Mach numbers indicated can easily be converted into flow velocities by a person skilled in the art for a known boiler temperature and known materials data. Likewise, a person skilled in the art can calculate the required admission pressure as a function of the indicated Mach number and the materials data.

The high entry velocity of the amine stream into the mixing zone serves, as indicated above, to achieve a very large velocity difference between amine- and phosgene-comprising feed streams. Furthermore, the system pressure and thus also the starting material concentrations and also the temperature are reduced locally by the high flow velocity, which leads to a reduction in the reaction rates and thus to a simplification of the mixing task.

To achieve very short mixing path lengths, efforts have to be made to select a likewise very high flow velocity of the phosgene-comprising feed stream, but without reducing the velocity difference between the amine- and phosgene-comprising feed streams too much. For this purpose, the cross-sectional area of the phosgene stream is selected so that a Mach number of from 0.2 to 2.0, preferably from 0.3 to 1.5, particularly preferably from 0.4 to 1.0, very particularly preferably from 0.5 to 1.0 and in particular from 0.7 to 1.0, is obtained.

The flow cross sections of the amine-comprising feed streams in the mixing unit according to the invention are preferably selected so that, firstly, a high operating stability is ensured and, secondly, very short mixing path lengths are maintained. Characteristic dimensions of from 0.5 to 50 mm, preferably from 0.75 to 25 mm, particularly preferably from 1 mm to 10 mm and very particularly preferably from 1 mm to 5 mm, are therefore selected for the inlet for the amine-comprising feed stream. Here, the characteristic dimension is the smallest dimension of the flow cross section, i.e., for example, in the case of a slit the slit width or in the case of a circular opening the opening diameter.

In the mixing device, the individual starting materials are preferably fed into the reactor at a flow velocity of from 20 to 400 meter/second, preferably from 25 to 300 meter/second, particularly preferably from 30 to 250 meter/second, very particularly preferably from 50 to 200 meter/second, in particular from >150 to 200 meter/second and especially from 160 to 180 meter/second.

In one possible embodiment of the invention, it can be useful to introduce the phosgene streams, in particular the outer phosgene stream, into the mixing space at a higher flow velocity than the amine stream which they surround, particularly preferably at at least 10 m/s more, very particularly preferably at least 20 m/s more and in particular at least 50 m/s more.

However, it can also be possible and useful to introduce the outer phosgene stream into the mixing space at a higher flow velocity than the amine stream and to introduce the inner phosgene stream at a lower flow velocity. This represents a further possible embodiment of the present invention.

In a preferred embodiment of the invention, it is useful to introduce the phosgene streams, in particular the outer phosgene stream, into the mixing space at a lower flow velocity than the amine stream which they surround, particularly preferably at at least 50 m/s less, very particularly preferably at least 60 m/s less, very particularly preferably 80 m/s less and especially at least 100 m/s less.

In a preferred embodiment of the present invention, the (n+1) slits for the phosgene streams are connected with a low pressure drop and without additional regulating devices to precisely one phosgene inlet so that the velocity at which the phosgene flows out of the (n+1) slits is approximately equal.

Likewise, the n slits of the amine streams are preferably connected with a low pressure drop and without additional regulating devices to precisely one amine inlet so that the velocity at which the amine flows out of the n slits is approximately equal.

However, it is also possible to connect each of the phosgene and/or amine streams of the slits to a separate regulated inlet, so that the velocities per inlet can be adjusted individually and independently of one another.

The starting materials enter the mixing space with a velocity vector. Here, the velocity vector can be divided into an axial direction component, a radial direction component and a tangential direction component. For the present purposes, the axial direction is the direction component of the velocity vector parallel to the longitudinal axis of the mixing space. The radial direction is the direction component of the velocity vector from outside to the longitudinal axis, i.e. making a right angle with the longitudinal axis. The tangential direction is the direction component of the velocity vector parallel to the boundary of the mixing space, i.e. a circular rotational motion.

To mix the feed streams, an improvement in the mixing established can be achieved by installation of mixing elements which produce a tangential velocity, for example in the inlet of the feed streams of the excess component into the mixing space. A suitable element which produces a tangential velocity would be, for example, a spirally twisted band (helix) let into the inlet, round or angular guide plates (guide vanes) or the like. The effect of the internals producing a tangential velocity is to increase the shear between flow laminar of differing composition in the flow in the nozzle.

To produce a tangential velocity, a tangential entry into the inlet of one or more feed streams or in the case of radial inflow of one or more feed streams a vane ring is also possible.

Furthermore, it can be useful to introduce the phosgene and amine streams into the mixing space with opposite tangential velocities, for example by introducing the phosgene streams into the mixing space with a clockwise tangential velocity viewed along the longitudinal axis of the reactor and introducing the amine stream between them with a counter clockwise tangential velocity.

The angle made by the resultant vector of the vectors of the tangential velocity and the vector of the axial velocity of the streams introduced in this way with the longitudinal axis of the reactor can be from 5 to 85°, preferably from 17 to 73°, particularly preferably from 30 to 60°, for the one set of streams, for example the phosgene streams, and from −5 to −85°, preferably from −17 to −73°, particularly preferably from −30 to −60°, for the other streams, for example the amine stream.

Furthermore, it is useful to introduce the streams into the mixing space with different radial velocities. Here, the resultant vector of the radial velocity vector and the axial velocity vector makes an angle with the longitudinal axis. This angle generally corresponds to the angle of the associated feed channel with the longitudinal axis of the mixing space. Here, a negative angle means introduction from the inside outward, a positive angle means introduction from the outside inward, an angle of 0° means flow parallel to the longitudinal axis of the mixing space and an angle of 90° means flow perpendicular to the longitudinal axis of the mixing space.

The outer phosgene stream can be fed through the mixing device into the mixing space at a radial angle of from 0 to 85°, preferably from 5 to 85°, particularly preferably from 7 to 65°, very particularly preferably from 15 to 35° and in particular from 18 to 30°.

The amine stream can be fed through the mixing device into the mixing space at a radial angle of from −50° to +50°, preferably from −25 to 25°, particularly preferably from −10 to 10° and very particularly preferably from −3 to +3°.

The inner phosgene stream can be fed through the mixing device into the mixing space at a radial angle of from 0 to −85°, preferably from −5 to −85°, particularly preferably from −7 to −65°, very particularly preferably from −15 to −35° and in particular from −18 to −30°.

It is advantageous for the outer phosgene stream and the amine stream to enclose a radial angle of from 1 to 60°, preferably from 7 to 50°, particularly preferably from 15 to 45° and particularly preferably from 18 to 35°, relative to one another.

It is also advantageous for the amine stream and the inner phosgene stream to enclose a radial angle of from 1 to 60°, preferably from 10 to 50°, particularly preferably from 15 to 45° and particularly preferably from 18 to 35°, relative to one another.

To achieve very complete conversion of the amine into the respective desired product, a mixing time of the phosgene-comprising feed stream with the amine-comprising feed stream of less than 10 ms, preferably less than 5 ms, particularly preferably less than 2 ms, very particularly preferably less than 1 ms and in particular less than 0.5 ms, is achieved by means of the measures described above. For the present purposes, the mixing time is the maximum time required by the fluid elements leaving the amine inlet for the phosgene/amine ratio in them to be greater than or equal to 4. The time is in each case counted from the point at which a fluid element exits from the amine inlet.

Reaction Space

The reaction space comprises the front region of the mixing space in which mixing of the gaseous mixture of phosgene, amine, if appropriate mixed with inert medium, predominantly takes place, which is generally accompanied by commencement of the reaction. Then, essentially only the reaction and at most a subordinate degree of mixing take place in the downstream part of the reaction space.

For the purpose of making a distinction, the mixing space can be considered to be the region of the reaction space in which mixing of the starting materials takes place to a degree of 99%. In a preferred embodiment of the present invention, the conversion in the mixing space, i.e. the consumption of the amine used, is less than 15%. Here, the degree of mixing is defined as the ratio of the difference between the locally averaged mixing fraction and the initial mixing fraction prior to mixing to the difference between the mean final mixing fraction after mixing and the initial mixing fraction prior to mixing. With regard to the concept of the mixing fraction, reference may be made, for example, to J. Warnatz, U. Maas, R. W. Dibble: Verbrennung, Springer Verlag, Berlin Heidelberg New York, 1997, 2nd edition, p. 134.

For the purposes of the present invention, the reactor is the engineering apparatus comprising the reaction space. All customary reaction spaces known from the prior art which are suitable for noncatalytic, single-phase gas reactions, preferably continuous noncatalytic, single-phase gas reactions, and withstand the moderate pressures required are possible here. Suitable materials for contact with the reaction mixture are, for example, metals such as steel, tantalum, silver or copper, glass, ceramic, enamels or homogeneous or heterogeneous mixtures thereof. Preference is given to using steel reactors. The walls of the reactor can be hydraulically smooth or profiled. Suitable profiles are, for example, grooves or corrugations.

It is generally possible to use the reactor construction types known from the prior art. Examples of reactors are known from EP-B1 289840, column 3, l. 49—column 4, l. 25, EP-B1 593334, WO 2004/026813, p. 3, l. 24—p. 6, l. 10, WO 03/045900, p. 3, l. 34—p. 6, l. 15, EP-A1 1275639, column 4, l. 17—column 5, l. 17 and EP-B1 570799, column 2, l. 1—column 3, l. 42, which are each expressly incorporated by reference into the present disclosure.

Preference is given to using tube reactors.

It is likewise possible to use essentially cuboidal reaction spaces, preferably plate reactors or plate reaction spaces. A particularly preferred plate reactor has a ratio of width to height of at least 2:1, preferably at least 3:1, particularly preferably at least 5:1 and in particular at least 10:1. The upper limit to the ratio of width to height depends on the desired capacity of the reaction space and is not restricted in principle. Reaction spaces having a ratio of width to height of up to 5000:1, preferably up to 1000:1, have been found to be industrially useful.

The reaction of phosgene with amine in the reaction space occurs at absolute pressures of from >0.1 bar to <20 bar, preferably from 0.5 bar to 15 bar and particularly preferably from 0.7 to 10 bar. In the case of the reaction of (cyclo)aliphatic amines, the absolute pressure is very particularly preferably in the range from 0.7 bar to 5 bar, in particular from 0.8 to 3 bar and especially from 1 to 2 bar.

In general, the pressure in the inlets into the mixing device is higher than the abovementioned pressure in the reactor. Depending on the choice of mixing device, this pressure decreases in the device. The pressure in the inlets is preferably from 20 to 2000 mbar higher, particularly preferably from 30 to 1000 mbar higher, than in the reaction space.

In one possible embodiment, the reactor comprises a bundle of reactors. In one possible embodiment, the mixing unit does not have to be an independent device, but instead it can be advantageous to integrate the mixer unit into the reactor. An example of an integrated unit as mixing unit and reactor are a tube reactor with flanged-on nozzles.

In the process of the invention, the reaction of phosgene with amine occurs in the gas phase. For the present purposes, reaction in the gas phase means that the feed streams and intermediates react with one another in the gaseous state to give the products and during the course of the reaction while passing through the reaction space remain in the gas phase to an extent of at least 95%, preferably at least 98%, particularly preferably at least 99%, very particularly preferably at least 99.5%, in particular at least 99.8% and especially at least 99.9%.

Intermediates are, for example, the monoaminomonocarbamoyl chlorides, dicarbamoyl chlorides, monoamino monoisocyanates and monoisocyanatomonocarbamoyl chlorides formed from the diamines and also the hydrochlorides of the amino compounds.

In the process of the invention, the temperature in the reaction space is selected so that it is above the boiling point of the diamine used, based on the pressure conditions prevailing in the reaction space. Depending on the amine used and the pressure set, a temperature in the reaction space of more than 200° C. is usually advantageous, preferably more than 260° C. and particularly preferably more than 300° C. In general, the temperature is up to 600° C., preferably up to 570° C.

The mean contact time of the reaction mixture in the process of the invention is generally from 0.001 second to <5 seconds, preferably from >0.01 second to <3 seconds, particularly preferably from >0.015 second to <2 seconds. In the case of the reaction of (cyclo)aliphatic amines, the mean contact time can very particularly preferably be from 0.015 to 1.5 seconds, in particular from 0.015 to 0.5 second, especially from 0.020 to 0.1 second and often from 0.025 to 0.05 second.

For the purposes of the present invention, the mean contact time is the time from the commencement of mixing of the starting materials until they leave the reaction space and go to the work-up stage. In a preferred embodiment, the flow in the reactor of the process of the invention has a Bodenstein number of more than 10, preferably more than 100 and particularly preferably more than 500.

In a preferred embodiment, the dimensions of the reaction space and the flow velocities are selected so that the reaction mixture displays turbulent flow, i.e. flow having a Reynolds number of at least 2300, preferably at least 2700, with the Reynolds number being calculated from the hydraulic diameter of the reaction space.

The gaseous reaction mixture preferably passes through the reaction space at a flow velocity of from 10 to 300 meter/second, preferably from 25 to 250 meter/second, particularly preferably from 40 to 230 meter/second, very particularly preferably from 50 to 200 meter/second, in particular from >150 to 190 meter/second and especially from 160 to 180 meter/second.

As a result of the turbulent flow, narrow residence time distributions with a low standard deviation of usually not more than 6% as described in EP 570799 and good mixing are achieved. Measures such as the constriction described in EP-A-593 334, which is also susceptible to blockage, are not necessary.

It can be useful to install flow equalizers as are known, for example from EP 1362847 A in the reactor.

The reaction volume can be heated/cooled via its outer surface. In order to build production plants having a high plant capacity, a plurality of reactor tubes can be connected in parallel. However, the reaction can also preferably be carried out adiabatically. This means that heating or cooling energy flows do not flow over the outer surface of the reaction volume as a result of technical measures.

In a preferred embodiment, the reaction conditions are selected so that the reaction gas at the exit from the reaction space has a phosgene concentration of more than 25 mol/m$^3$, preferably from 30 to 50 mol/m$^3$. Furthermore, an inert medium concentration of more than 25 mol/m$^3$, preferably from 30 to 100 mol/m$^3$, is generally present at the exit from the reaction space.

The reaction space can be divided structurally into essentially four longitudinal sections along the longitudinal axis of the reactor in the direction of flow:
 a first, usually short section downstream of the starting material feed facility having a length of $L_1$,
 a second section having a length of $L_2$,
 a third section having a length of $L_3$ followed by
 a fourth section having a length of $L_4$ which represents a tube reactor without internal displacement bodies and is joined by a quench (see below).

The term reaction space describes the volume in which at least 98% of the conversion, i.e. the consumption of the amine used, takes place, preferably at least 99%, particularly preferably 99.5%, very particularly preferably 99.7%, in particular 99.9% and especially 99.99%.

The individual parameters which describe the geometries in these up to four sections are denoted by the indices 1, 2, 3 and 4.

The main characterizing parameter is R, namely the total diameter of the tube reactor, i.e. from interior wall to interior wall.

A further characterizing parameter is the angle $\alpha$, where $\alpha$ is the angle made by the outer wall with the longitudinal axis of the tube reactor.

A positive angle $\alpha$ thus denotes an outer wall of the tube reactor which widens in the flow direction, while a negative angle $\alpha$ indicates a narrowing.

The parameter R indirectly determines the area F of the reactor through which flow occurs, and a determines the way in which it changes in the flow direction.

It goes without saying that the values of R coincide at the transitions from one section to the other. The changes in the individual values in each case relate to the changes within the sections.

The present invention further provides various preferred constructions of the reaction space which differ in terms of the size of the cross-sectional areas along the longitudinal direction of the axis in the direction of flow:

In the first alternative construction (FIG. 3, depiction a), the area F through which flow occurs does not change along the reactor, i.e. there is no structural distinction between sections and instead there is only a single section 1. In this, $R_1$ remains constant over the entire length of the reactor, and $\alpha_1$ is 0°. The entire reactor is thus configured as a mixing space, preferably a rectangular mixing space.

In a second alternative construction (FIG. 3, depiction b), the area $F_1$ through which flow occurs enlarges in a section 1 directly after the streams have been combined and then remains constant in a second section 2.

Figure 3A:
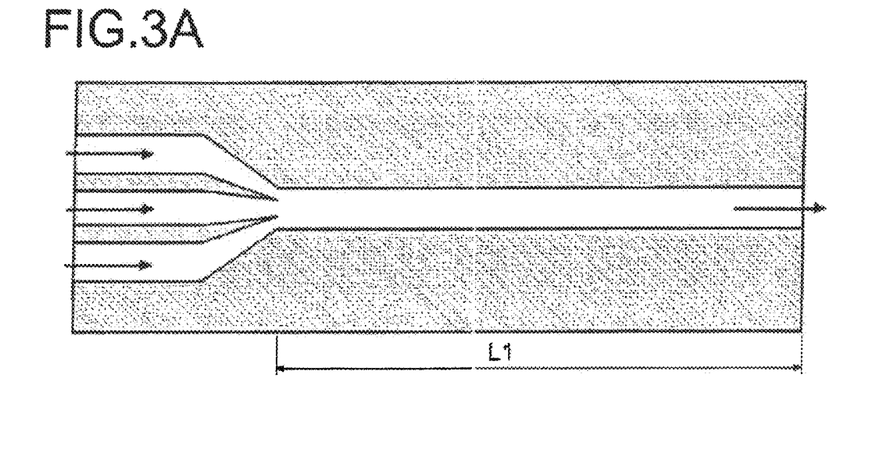
Figure 3B:
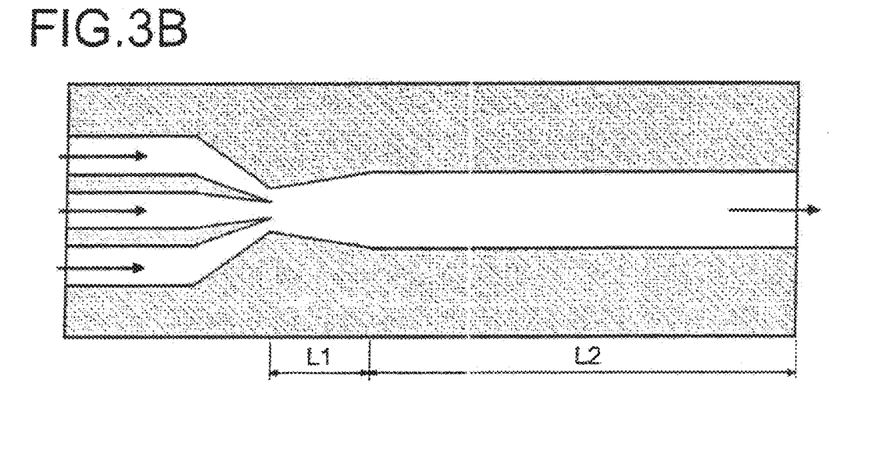

This can be achieved by increasing $R_1$. In this case the angle $\alpha_1$ is from 0.0001 to 10°, preferably from 0.0002 to 8°, particularly preferably from 0.0003 to 7° and very particularly preferably from 0.0003 to 6°.

In section 2, $R_2$ then remains constant and $\alpha_2$ is 0°.

In a third alternative construction (FIG. 3, depiction c), the area $F_1$ remains constant in a section 1 and widens in the second section before remaining constant again in the third section.

Figure 3C:
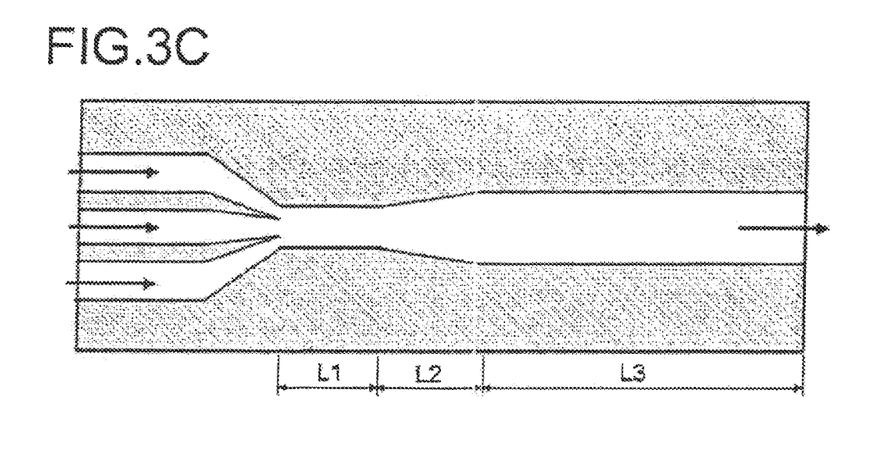

In this case, $R_1$ remains constant in section 1, and $\alpha_1$ is 0° in this section.

In the second section, $F_2$ increases, which is achieved by an increase in $R_2$, and means that $\alpha_2$ is, for example, from 0.0001 to 10°, preferably from 0.0002 to 8°, particularly preferably from 0.0003 to 7° and very particularly preferably from 0.0003 to 6°.

In the third section, $F_3$ remains constant, which is achieved by $R_3$ being constant and $\alpha_3$ being 0°.

In a fourth alternative construction (FIG. 3, depiction d), the area $F_1$ is kept constant in a section 1, $F_2$ in the section 2 is then reduced and $F_3$ is increased in section 3 and is kept constant in section 4.

Figure 3D:
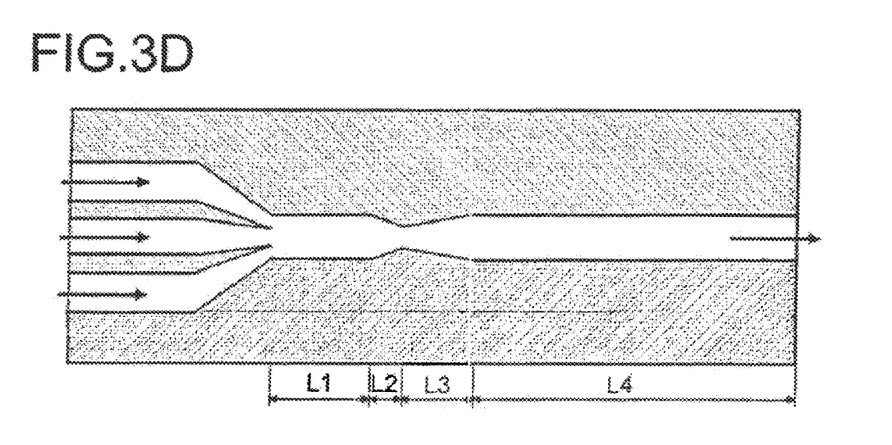

This is achieved by keeping $R_1$ constant and maintaining $\alpha_1$ at 0°.

In the second section, $F_2$ decreases, which is achieved by means of a decrease in $R_2$. For this purpose, $\alpha_2$ is, for example, less than 0° and more than −90°, preferably from −7 to −65°, particularly preferably from −15 to −35° and very particularly preferably from −20 to −30°.

In the third section, $F_3$ increases, which is achieved by means of an increase in $R_3$, which means that $\alpha_3$ is, for example, from 0.0001 to 10°, preferably from 0.0002 to 8°, particularly preferably from 0.0003 to 7° and very particularly preferably from 0.0003 to 6°.

In the fourth section, $F_4$ then remains constant; for this purpose, $R_4$ in section 4 remains constant and $\alpha_4$ is 0°.

In a fifth alternative construction (FIG. 3, depiction e), the area $F_1$ is reduced in a first section, $F_2$ is increased in the second section and $F_3$ is kept constant in the third section.

Figure 3E:
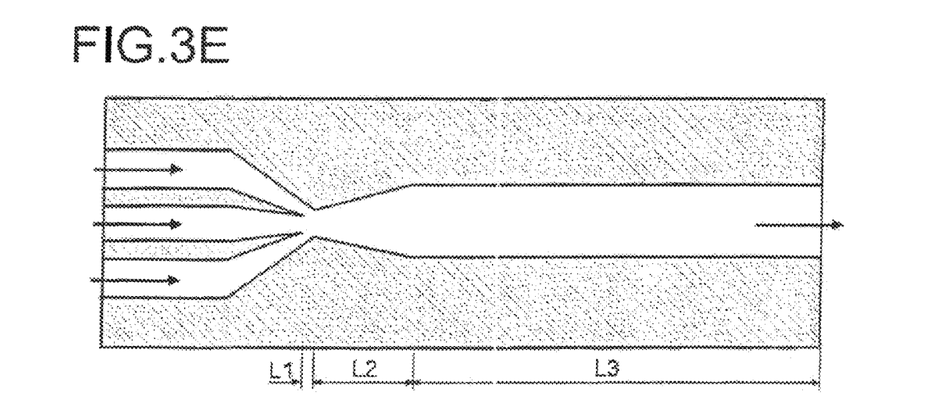

In the first section, $F_1$ is reduced, which is achieved by a decrease in $R_1$. $\alpha_1$ is, for example, less than 0° and more than −90°, preferably from −7 to −65°, particularly preferably from −15 to −35° and very particularly preferably from −20 to −30°.

In the second section, $F_2$ increases, which is achieved by an increase in $R_2$, which means that $\alpha_2$ is, for example, from 0.0001 to 10°, preferably from 0.0002 to 8°, particularly preferably from 0.0003 to 7° and very particularly preferably from 0.0003 to 6°.

In section 3, $R_3$ remains constant and $\alpha_3$ it 0°.

In the sixth alternative construction (FIG. 3, depiction f), the area $F_1$ is reduced, remains constant in section two, is increased again in section 3 and then remains constant again in the fourth section.

Figure 3F:
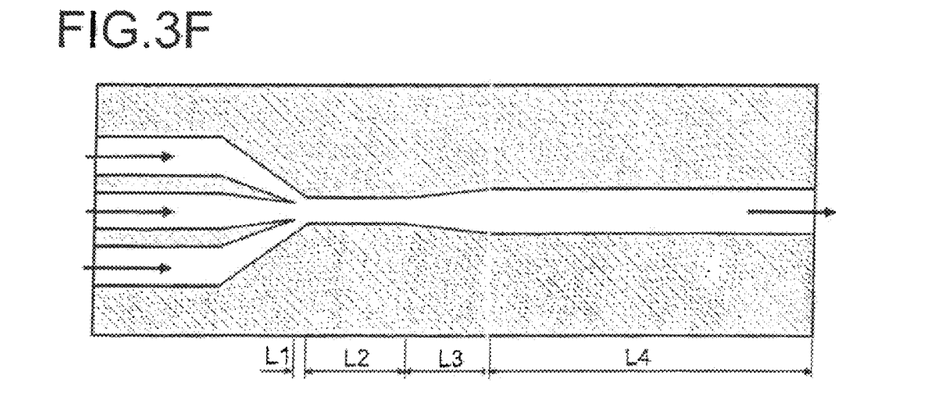

In the first section, $F_1$ decreases, which is achieved by a decrease in $R_1$. $\alpha_1$ is, for example, less than 0° and more than −90°, preferably from −7 to −65°, particularly preferably from −15 to −35° and very particularly preferably from −20 to −30°.

In section 2, $R_2$ remains constant and $\alpha_2$ is 0°.

In the third section, $F_3$ increases, which is achieved by an increase in $R_3$, which means that $\alpha_3$ is, for example, from 0.0001 to 10°, preferably from 0.0002 to 8°, particularly preferably from 0.0003 to 7° and very particularly preferably from 0.0003 to 6°.

In section 4, $R_4$ remains constant and $\alpha_4$ is 0°.

In the sixth alternative construction, the length of section 2 is chosen differently according to the amine used: in the case of isocyanates which have a strong tendency to form deposits, e.g. (cyclo)aliphatic isocyanates and in particular hexamethylene 1,6-diisocyanate, a short section 2 is preferred.

The length of zone 2, i.e. $L_2$, is generally less than 30 times, preferably less than 15 times, particularly preferably less than 10 times, very particularly preferably less than 6 times, in particular less than five times and especially less than three times, the resulting gap width ($R_2$). $L_2$ is often less than twice and even less than once the gap width ($R_2$).

In contrast, in the case of isocyanates which display little tendency to form deposits, for example aromatic isocyanates and in particular tolylene diisocyanate, a very long section 2 is preferred.

In the case of such isocyanates, the length of zone 2 is greater than the resulting gap width ($R_2$), preferably greater than 5 times, particularly preferably greater than 10 times, very particularly preferably greater than 15 times and especially greater than 30 times the resulting gap width ($R_2$).

The length of the last section in each case which has a constant area F, i.e. in the sixth alternative construction, $L_4$, is selected so that, firstly, the desired mean contact time in the reactor is achieved and, secondly, an $L_4/(2*R_4)$ ratio of greater than 2, preferably greater than 4, particularly preferably greater than 6, very particularly preferably greater than 10 and especially greater than 15, is obtained.

In sections having a constant or increasing area, F is selected so that the mean velocity of the reaction mixture is generally greater than 60 m/s, preferably greater than 100 m/s, particularly preferably greater than 160 m/s and very particularly preferably greater than 180 m/s and especially greater than 200 m/s. In addition, F is selected so that the mean velocity is generally less than 250 m/s, preferably less than 240 m/s, particularly preferably less than 230 m/s, very particularly preferably less than 220 m/s and especially less than 210 m/s.

The changes in the parameter R can be linear or nonlinear within the sections. In the case of a linear change, the angle $\alpha$ remains constant within the section and changes only at the transitions between the sections. In the case of a nonlinear change, the increase or decrease within the sections can be concave, i.e. curved into the flow space, convex, i.e. curved away from the flow space, or mixed concave/convex or convex/concave. A concave change means that the angle $\alpha$ increases or becomes more positive in the direction of flow. Preference is given to a linear change.

The transitions between the respective sections 1 to 4 can independently be sharp or rounded. Preference is given to a rounded design.

The alternative constructions are shown as preferred embodiments in FIG. 3 (not to scale) and depicted in a fashion analogous to the numbering in FIG. 1a. The alternative construction of FIG. 3f is particularly preferred:

Around the slit for introduction of the amine 2 there are two surrounding slits 1 for introduction of phosgene. The reaction space ¾ is bounded by an outer reactor wall 5 and divided along the direction in which the reaction proceeds into four sections having lengths of $L_1$, $L_2$, $L_3$ and $L_4$, which differ in the area through which flow occurs. Along the first section, immediately after mixing of the feed streams, the area $F_1$ through which flow occurs is decreased by reducing $R_1$, remains constant in section 2, increases again in section 3 by means of an increase in $R_3$ and then remains constant in the fourth section.

The volume of the reactor through which flow occurs can be filled with static mixers, for example ordered packing, random packing, meshes, perforated plates or slotted plates, but the volume is preferably mostly free of internals.

The installation of guide plates in the reaction space is also conceivable. A suitable, turbulence-generating element would be, for example, an inserted spirally twisted band, round or angular oblique plates or the like.

To obtain short mixing path lengths and thus short mixing times even in the case of large amine and phosgene flows as are customary in isocyanate production on an industrial scale, many small mixing nozzles with subsequent mixing and reaction zone can be connected in parallel, with the parallel units being separated from one another by walls. The advantage of this process variant is a more favorable length-to-diameter ratio of the mixing and reaction zones. The greater this ratio, the more favorable (narrower) the residence time distribution of the stream. Thus, at a given residence time and flow velocity, the length-to-diameter ratio can be increased and thus the residence time distribution can also be narrowed by means of many parallel units. To keep the outlay in terms of apparatus small, the individual reaction zones open into a joint after-reaction zone in which the residual conversion of the amine then occurs.

After the reaction, gaseous reaction mixture is preferably scrubbed with a solvent (quench) at temperatures of greater than 130° C. Preferred solvents are hydrocarbons which may optionally be substituted by halogen atoms, for example hexane, benzene, nitrobenzene, anisole, chlorobenzene, chlorotoluene, o-dichlorobenzene, trichlorobenzene, diethyl isophthalate (DEIP), tetrahydrofuran (THF), dimethylformamide (DMF), xylene, chloronaphthalene, decahydronaphthalene and toluene. Particular preference is given to using monochlorobenzene as solvent. The isocyanate can also be used as solvent. In the scrub, the isocyanate is selectively transferred into the scrubbing solution. The remaining gas and the scrubbing solution obtained are subsequently separated, preferably by means of rectification, into isocyanate, solvent, phosgene and hydrogen chloride.

After the reaction mixture has been reacted in the reaction space, it is conveyed into the work-up apparatus with quench. This is preferably a scrubbing tower in which the isocyanate formed is separated off from the gaseous mixture by condensation into an inert solvent, while excess phosgene, hydrogen chloride and if appropriate the inert medium pass through the work-up apparatus in gaseous form. The temperature of the inert solvent is preferably kept above the dissolution temperature of the carbamyl chloride corresponding to the amine in the quenching medium selected. The temperature of the inert solvent is particularly preferably kept above the melting point of the carbamyl chloride corresponding to the amine.

In general, the pressure in the work-up apparatus is lower than in the reaction space. The pressure is preferably from 50 to 500 mbar lower, particularly preferably from 80 to 150 mbar lower, than in the reaction space.

The scrub can be carried out, for example, in a stirred vessel or in other conventional apparatuses, e.g. in a column or a mixer-settler apparatus.

In process engineering terms, all extraction and scrubbing processes and apparatuses known per se, e.g. those described in Ullmann's Encyclopedia of Industrial Chemistry, 6th ed., 1999 Electronic Release, Chapter: Liquid—Liquid Extraction—Apparatus, can be used for a scrub in the process of the invention. For example, these can be single-stage or multistage, preferably single-stage, extractions and also cocurrent or countercurrent extractions, preferably countercurrent extractions.

A suitable quench is known, for example, from EP-A1 1403248, column 2, l. 39—column 3, l. 18, which is expressly incorporated by reference into the present disclosure.

In this quench zone, the reaction mixture, which consists essentially of the isocyanates, phosgene and hydrogen chloride, is mixed intensively with the liquid sprayed in. Mixing is carried out so that the temperature of the reaction mixture is reduced from 200-570° C. to 100-200° C., preferably to 140-180° C., and the isocyanate comprised in the reaction mixture goes completely or partly over into the liquid droplets sprayed in as a result of condensation while the phosgene and the hydrogen chloride remain essentially completely in the gas phase.

The proportion of the isocyanate comprised in the gaseous reaction mixture which goes over into the liquid phase in the quench zone is preferably from 20 to 100% by weight, particularly preferably from 50 to 99.5% by weight and in particular from 70 to 99% by weight, based on the isocyanate comprised in the reaction mixture.

The reaction mixture preferably flows through the quench zone from the top downward. Below the quench zone, there is a collection vessel in which the liquid phase is precipitated, collected and removed from the reaction space via an outlet and is subsequently worked up. The remaining gas phase is removed from the reaction space via a second outlet and is likewise worked up.

The quench can, for example, be carried out as described in EP 1403248 A1 or as described in the International patent application WO 2005/123665.

The liquid droplets are for this purpose produced by means of single- or two-fluid atomizer nozzles, preferably single-fluid atomizer nozzles, and, depending on the embodiment, form a spray cone having an angle of from 10 to 140°, preferably from 10 to 120°, particularly preferably from 100 to 100°.

The liquid which is sprayed in via the atomizer nozzles has to have a good solvent capability for isocyanates. Preference is given to using organic solvents. In particular, use is made of aromatic solvents which may be substituted by halogen atoms.

In a particular embodiment of the process, the liquid sprayed in is a mixture of isocyanates, a mixture of isocyanates and solvent or isocyanate, with the quenching liquid used in each case being able to have proportions of low boilers such as HCl and phosgene. Preference is given to using the isocyanate which is prepared in the respective process. Since the reaction is stopped by the reduction in temperature in the quench zone, secondary reactions with the isocyanates sprayed in can be ruled out. The advantage of this embodiment is, in particular, that it is not necessary to separate off the solvent.

In an alternative preferred embodiment, the inert medium which is used together with at least one of the starting materials and the solvent which is used in the quench are the same compound. Monochlorobenzene is very particularly preferably used in this case.

Small amounts of by-products which remain in the isocyanate can be separated from the desired isocyanate by means of additional rectification, by stripping with an inert gas or by crystallization, preferably by rectification.

In the subsequent optional purification step, the isocyanate is separated off from the solvent, preferably by distillation. Here too, the removal of residual impurities comprising hydrogen chloride, inert medium and/or phosgene can be carried out as described, for example, in DE-A1 10260092.

In a particular embodiment of the process of the invention, the phosgene-comprising and amine-comprising feed streams are each fed into the mixing zone via at least one slit-like opening. The openings conveying phosgene and amine are preferably arranged in an alternating fashion. The amine slits are preferably arranged so that at least one phosgene-conveying opening is present between them and the mixing zone wall. The amine and phosgene slits can have a constant or a variable width. Furthermore, the imaginary central lines of the slit can describe any curves. They preferably describe circles, triangles or quadrilaterals in general, ellipses or straight lines. FIGS. 1a and 1b show a flat embodiment of the mixing nozzle in which the amine stream to be fed in through a straight slit is surrounded by a circumferential enveloping phosgene stream, so that premature contact of amine-rich reaction mixture with the wall is avoided. Intensive mixing of the starting materials occurs in the mixing zone. The mixing zone is then followed by a reaction zone.

Figure 2A:
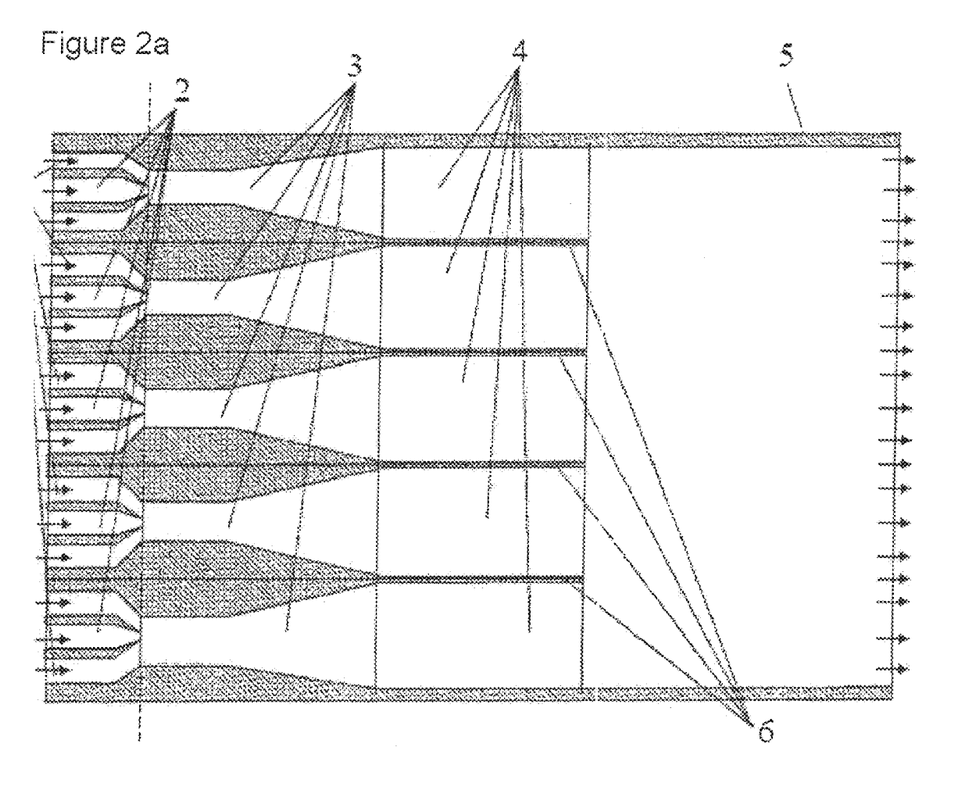
FIGS. 2a and 2b show the mixing zone and reaction zone of a process according to the invention in which mixing of amine and phosgene is achieved by means of a plurality of stacked single nozzles.
Figure 2B:
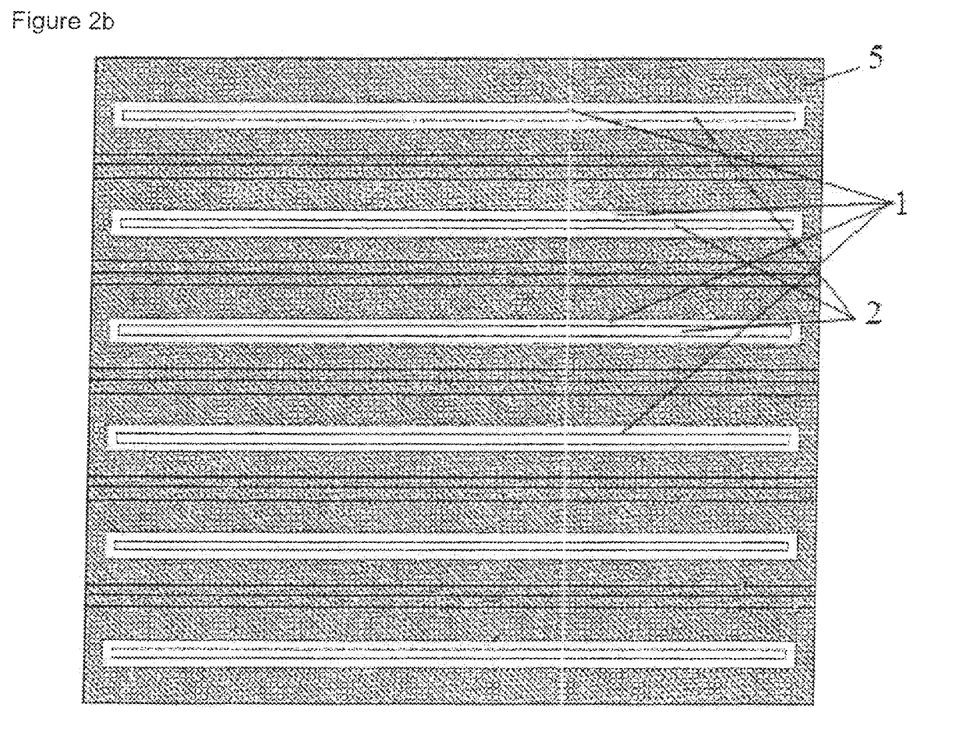

In a further preferred embodiment of the process of the invention, a plurality of mixing nozzles are arranged or stacked in parallel. Here, each mixing nozzle has at least one amine inlet and one phosgene inlet. Each mixing nozzle has a mixing zone and reaction zone, with the individual mixing zones and reaction zones being separated from one another by walls. The individual reaction zones then open into a joint after-reaction zone in which residual conversion of the amine is then achieved. The amine and phosgene inlets can have any shapes. Thus, the inlets can be, for example, circular, elliptical, triangular, in the form of a quadrilateral or in the form of a polygon in general or else be slit-shaped, with the imaginary middle line of the slit being able to have any shape. Preference is given to slit-like openings. FIGS. 2a and 2b show the mixing zone and reaction zone of a process according to the invention in which mixing of amine and phosgene is achieved by means of a plurality of stacked single nozzles. Each of the single nozzles is followed by a mixing zone and a reaction zone. The mixing zones are separated from one another by walls. Likewise, the reaction zones are separated by walls. Downstream of the individual reaction zones, there is a joint after-reaction zone.

In FIGS. 1a, 1b, 2a and 2b, the reference numerals have the following meanings:
1: phosgene inlet
2: amine inlet
3: mixing zone
4: reaction zone
5: reactor walls
6: dividing wall

The invention claimed is:

1. A process for preparing isocyanates, which comprises reacting in the gas phase at least one amine stream with at least one phosgene stream in a reactor and introducing at least one amine stream and at least one phosgene stream into the reactor each via at least one slit for mixing arranged in parallel,
wherein said at least one slit has a ratio of width to height of at least 2:1.

2. The process according to claim 1, wherein the isocyanate is selected from the group consisting of 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures.

3. The process according to claim 1, wherein at least one inert medium selected from the group consisting of nitrogen, helium, argon, chlorobenzene, chlorotoluene, o-dichlorobenzene, toluene, xylene, chloronaphthalene, decahydronaphthalene, carbon dioxide and carbon monoxide is present.

4. The process according to claim 3, wherein the gas volume ratio of inert medium to amine or to phosgene is more than 0.0001 to 30.

5. The process according to claim 1, wherein the temperature in the process is from 200 to 600° C.

6. The process according to claim 1, wherein a molar ratio of phosgene to amino groups of from 1.1:1 to 20:1 is set.

7. The process according to claim 1, wherein a phosgene stream is introduced into the reactor as outermost stream at the outer wall.

8. The process according to claim 1, wherein the ratio of the total area of the amine streams to the total area of the phosgene streams is greater than 0.00002 and less than 5.

9. The process according to claim 1, wherein the at least one amine stream and the at least one phosgene stream are fed into the reactor at a flow velocity of from 20 to 400 meter/second.

10. The process according to claim 1, wherein the amine is introduced through a slit which is flanked on both longitudinal sides by slits through which phosgene is introduced.

11. The process according to claim 10, wherein amine is introduced through n slits and phosgene is introduced through (n+1) slits, with each of the n slits through which amine is introduced being flanked by 2 slits through which phosgene is introduced.

12. The process according to claim 1, wherein amine is introduced through an inner slit which is surrounded on all sides by a contiguous slit through which phosgene is introduced.

13. The process according to claim 12, wherein the outer slit through which phosgene is introduced is flanked by a further contiguous or noncontiguous slit for introduction of amine and this is in turn surrounded on all sides by a contiguous slit through which phosgene is introduced.

14. The process according to claim 1, wherein the mixing time of the phosgene-comprising feed stream with the amine-comprising feed stream is less than 10 ms.

15. The process according to claim 1, wherein the mean contact time of the reaction mixture is from 0.001 second to <5 seconds.

16. The process according to claim 1, wherein the flow in the reactor has a Bodenstein number of more than 10.

17. The process according to claim 1, wherein the flow of the reaction mixture has a Reynolds number of at least 2300.

18. The process according to claim 1, wherein the conversion of amine in the space in which mixing of the starting materials takes place to an extent of 99% is not more than 15%.

19. The process according to claim 1, where in the amine stream comprises at least one amine selected from the group consisting of an aliphatic monoamine, a cycloaliphatic monoamine, an aromatic monoamine, an aliphatic diamine, a cycloaliphatic diamine, an aromatic diamine, an aliphatic triamine, a cycloaliphatic diamine, an aromatic diamine, an aliphatic higher-functionality amine, a cycloaliphatic higher-functionality amine, and an aromatic higher-functionality amine.

20. The process according to claim 1, wherein said at least one slit has a slit width of from 0.5 to 50 mm.

21. The process according to claim 1, wherein said at least one slit has a slit width of from 1 to 10 mm.

22. The process according to claim 1, wherein said at least one slit has a ratio of width to height of at least 5:1.

23. The process according to claim 1, wherein said at least one slit has a ratio of width to height of less than 500:1.

24. The process according to claim 1, wherein said at least one slit has a ratio of width to height of less than 100:1.

25. The process according to claim 1, wherein at least one amine stream and at least one phosgene stream are introduced via a two component nozzle.

* * * * *